US010835758B2

(12) United States Patent
Choi et al.

(10) Patent No.: US 10,835,758 B2
(45) Date of Patent: Nov. 17, 2020

(54) ORGANIC LIGHT-EMITTING DEVICE FOR LIGHT THERAPY FOR WOUND HEALING AND CELL PROLIFERATION AND MANUFACTURING METHOD THEREOF

(71) Applicants: Korea Advanced Institute of Science and Technology, Daejeon (KR); Seoul National University Bundang Hospital, Seongnam-si (KR)

(72) Inventors: Kyung Cheol Choi, Daejeon (KR); Yong Min Jeon, Daejeon (KR); Kyoung Chan Park, Seongnam-si (KR); Hye Ryung Choi, Seongnam-si (KR)

(73) Assignees: Korea Advanced Institute of Science and Technology, Daejeon (KR); Seoul National University Bundang Hospital, Seongnam-si (KR)

( * ) Notice: Subject to any disclaimer, the term of this patent is extended or adjusted under 35 U.S.C. 154(b) by 5 days.

(21) Appl. No.: 15/860,869

(22) Filed: Jan. 3, 2018

(65) Prior Publication Data

US 2018/0272150 A1 Sep. 27, 2018

(30) Foreign Application Priority Data

Mar. 22, 2017 (KR) .................. 10-2017-0035961

(51) Int. Cl.
*A61N 5/06* (2006.01)
*H01L 51/50* (2006.01)
*H01L 51/52* (2006.01)

(52) U.S. Cl.
CPC ......... *A61N 5/0624* (2013.01); *A61N 5/0616* (2013.01); *H01L 51/5064* (2013.01);
(Continued)

(58) Field of Classification Search
CPC .......... A61N 2005/0653; A61N 5/0624; A61N 5/0625; A61N 5/0616; H01L 51/5068;
(Continued)

(56) References Cited

U.S. PATENT DOCUMENTS 9,240,435 B2 * 1/2016 Yoshida ............... H01L 27/3211
2013/0103123 A1 * 4/2013 Khan ..................... A61N 5/0624
607/90

(Continued)

FOREIGN PATENT DOCUMENTS

JP 20176347 A 1/2017
KR 1020090111967 A 10/2009
(Continued)

*Primary Examiner* — Christine A Enad
(74) *Attorney, Agent, or Firm* — The Webb Law Firm (57) ABSTRACT

Disclosed is an organic light-emitting device for light therapy for wound healing and cell proliferation, including: a substrate; an organic light-emitting device layer formed on the substrate and emitting red light; and a heat sink layer formed on the organic light-emitting device layer, which forms a red organic light-emitting device emitting red light in a stacking structure including a heat sink layer to generate light in a form of a planar light source which can be driven at a low temperature, thereby solving a problem of a burn and can perform light therapy through close contact with the skin.

14 Claims, 10 Drawing Sheets

(52) U.S. Cl.
CPC ........ *H01L 51/5072* (2013.01); *H01L 51/529* (2013.01); *H01L 51/5215* (2013.01); *H01L 51/5234* (2013.01); *A61N 5/0603* (2013.01); *A61N 2005/0653* (2013.01); *H01L 51/5016* (2013.01); *H01L 51/5056* (2013.01); *H01L 51/5265* (2013.01); *H01L 2251/558* (2013.01)

(58) Field of Classification Search
CPC ............. H01L 51/5064; H01L 51/5072; H01L 51/5215; H01L 51/5234
See application file for complete search history.

(56) References Cited

U.S. PATENT DOCUMENTS

| | | | | |
|---|---|---|---|---|
| 2015/0060811 | A1* | 3/2015 | Shiratori | H01L 51/5265 257/40 |
| 2015/0087685 | A1* | 3/2015 | Khan | A61N 5/062 514/410 |
| 2016/0101294 | A1* | 4/2016 | Sun | A61N 5/0616 607/88 |
| 2016/0325113 | A1* | 11/2016 | Khan | A61N 5/062 |

FOREIGN PATENT DOCUMENTS

| | | |
|---|---|---|
| KR | 1020140069443 A | 6/2014 |
| KR | 101660388 B1 | 9/2016 |

\* cited by examiner

ORGANIC LIGHT-EMITTING DEVICE FOR LIGHT THERAPY FOR WOUND HEALING AND CELL PROLIFERATION AND MANUFACTURING METHOD THEREOF

CROSS-REFERENCE TO RELATED APPLICATION

This application claims priority to Korean Patent Application No. 10-2017-0035961 filed Mar. 22, 2017, the disclosure of which is hereby incorporated in its entirety by reference.

TECHNICAL FIELD

The present invention relates to an organic light-emitting device for light therapy for wound healing and cell proliferation and a manufacturing method thereof.

BACKGROUND ART

Currently, in a medical field, light therapy is attracting attention as a means for promotion of health or therapy. The light therapy is a technique that absorbs light into the skin of a human body to activate, regenerate, or destroy specific tissues in the skin. In particular, it is widely known that there are generally effects on wound healing and cell proliferation in red to infra red regions in the 600 to 900 nm region, and research and commercialization are actively progressed using a 633 nm LED.

Since a III-V compound semiconductor based LED shows a form of a very small point light source, the III-V compound semiconductor based LED is disadvantageous in uniformly irradiating a large area. Therefore, in order to cover a wide area with an LED light source, multiple LEDs are generally arranged in an array form, and there may be a limit in terms of cost and uniformity.

There is a problem in that when a predetermined target amount of light is to be produced in a very small area, heat may be concentrated at one point depending on high current density, and when light is irradiated to an application field which directly contacts the skin, etc., or an object which is weakest to a temperature, such as a cell, etc., a problem may be caused. Since it is fundamentally difficult to attach a light therapy apparatus using an LED light source having a hard characteristic to the human body and it is difficult to carry the light therapy apparatus due to inflexibility and a bulky characteristic, the therapy can be performed only at a specific place such as a hospital. As a result, the therapy is performed at a distance, therapy performance is naturally reduced, and there is a possibility of side effects due to irradiation of the light to undesired portions such as eyes.

SUMMARY OF THE INVENTION

The present invention has been made in an effort to provide an organic light-emitting device for light therapy for wound healing and cell proliferation, which manufactures a red organic light-emitting device in a stacking structure including a heat sink layer to generate light in a form of a planar light source which can be driven at a low temperature, thereby solving a problem of a burn and can perform light therapy through close contact with the skin, and have advantages such as thin, light, flexible, and inexpensive characteristics and provide enhanced wound healing and cell proliferation effects compared with an LED in the related art.

The present invention has also been made in an effort to provide a manufacturing method of an organic light-emitting device for light therapy for wound healing and cell proliferation, which manufactures a red organic light-emitting device in a stacking structure including a heat sink layer to generate light in a form of a planar light source which can be driven at a low temperature, thereby solving a problem of a burn and can perform light therapy through close contact with the skin, have advantages such as thin, light, flexible, and inexpensive characteristics and provide enhanced wound healing and cell proliferation effects compared with an LED in the related art.

An exemplary embodiment of the present invention provides an organic light-emitting device for light therapy for wound healing and cell proliferation, including: a substrate; an organic light-emitting device layer formed on the substrate and emitting red light; and a heat sink layer formed on the organic light-emitting device layer.

In the organic light-emitting device for light therapy for wound healing and cell proliferation, the substrate may be transparent or translucent.

In the organic light-emitting device for light therapy for wound healing and cell proliferation, the organic light-emitting device layer may include a first encapsulation layer formed on the substrate, a first electrode layer formed on the first encapsulation layer, a hole injection layer formed on the first electrode layer, a hole transport layer formed on the hole injection layer, an organic light-emitting layer formed on the hole transport layer and emitting red light, an electron transport layer formed on the organic light-emitting layer, an electron injection layer formed on the electron transport layer, a second electrode layer formed on the electron injection layer, and a second encapsulation layer formed on the second electrode layer.

In the organic light-emitting device for light therapy for wound healing and cell proliferation, the first electrode layer may be transparent or translucent.

In the organic light-emitting device for light therapy for wound healing and cell proliferation, the hole transport layer may have thickness of 50 to 100 nm and a peak wavelength of the red light may be changed according to the thickness of the hole transport layer.

In the organic light-emitting device for light therapy for wound healing and cell proliferation, the organic light-emitting layer may have a thickness of 10 to 100 nm and emit red light having a wavelength of 600 to 750 nm.

In the organic light-emitting device for light therapy for wound healing and cell proliferation, the organic light-emitting layer may be made of one selected from a group consisting of $Ir(piq)_3$, $Ir(tiq)_3$, $Ir(fliq)_3$, $Ir(btpy)_3$, and $Ir(t-5t-py)_3$.

In the organic light-emitting device for light therapy for wound healing and cell proliferation, the second electrode layer may totally reflect light.

In the organic light-emitting device for light therapy for wound healing and cell proliferation, the heat sink layer may have a thickness of 1 to 500 nm and may be made of one selected from a group consisting of a carbon-based material, a metal-based material, and graphene.

Another exemplary embodiment of the present invention provides an organic light-emitting device for light therapy for wound healing and cell proliferation, including: a substrate; a heat sink layer formed on the substrate; and an organic light-emitting device layer formed on the heat sink layer and emitting red light.

In the organic light-emitting device for light therapy for wound healing and cell proliferation, the organic light-emitting device layer may include a second encapsulation layer formed on the heat sink layer, a second electrode layer formed on the second encapsulation layer, an electron injection layer formed on the second electrode layer, an electron transport layer formed on the electron injection layer, an organic light-emitting layer formed on the electron transport layer and emitting the red light, a hole transport layer formed on the organic light-emitting layer, a hole injection layer formed on the hole transport layer, a first electrode layer formed on the hole injection layer, and a first encapsulation layer formed on the first electrode layer.

In the organic light-emitting device for light therapy for wound healing and cell proliferation, the first electrode layer may be transparent or translucent.

In the organic light-emitting device for light therapy for wound healing and cell proliferation, the hole transport layer may have thickness of 50 to 100 nm and a peak wavelength of the red light may be changed according to the thickness of the hole transport layer.

In the organic light-emitting device for light therapy for wound healing and cell proliferation, the organic light-emitting layer may have a thickness of 10 to 100 nm and emit red light having a wavelength of 600 to 750 nm.

In the organic light-emitting device for light therapy for wound healing and cell proliferation, the organic light-emitting layer may be made of one selected from a group consisting of $Ir(piq)_3$, $Ir(tiq)_3$, $Ir(fliq)_3$, $Ir(btpy)_3$, and $Ir(t-5t-py)_3$.

In the organic light-emitting device for light therapy for wound healing and cell proliferation, the second electrode layer may totally reflect light.

In the organic light-emitting device for light therapy for wound healing and cell proliferation, the heat sink layer may have a thickness of 1 to 500 nm and may be made of one selected from a group consisting of a carbon-based material, a metal-based material, and graphene.

Yet another exemplary embodiment of the present invention provides a manufacturing method of an organic light-emitting device for light therapy for wound healing and cell proliferation, including: (a) forming an organic light-emitting device layer emitting red light on a substrate; and (b) forming a heat sink layer on the organic light-emitting device layer.

In the manufacturing method of an organic light-emitting device for light therapy for wound healing and cell proliferation, the substrate may be transparent or translucent.

In the manufacturing method of an organic light-emitting device for light therapy for wound healing and cell proliferation, the forming of the organic light-emitting device layer may include (a-1) forming a first encapsulation layer on the substrate, (a-2) forming a first electrode layer on the first encapsulation layer, (a-3) forming a hole injection layer on the first electrode layer, (a-4) forming a hole transport layer on the hole injection layer, (a-5) forming an organic light-emitting layer emitting red light on the hole transport layer, (a-6) forming an electron transport layer on the organic light-emitting layer, (a-7) forming an electron injection layer on the electron transport layer, (a-8) forming a second electrode layer on the electron injection layer, and (a-9) forming a second encapsulation layer on the second electrode layer.

According to an exemplary embodiment of the present invention, an organic light-emitting device for light therapy for wound healing and cell proliferation shows a more excellent effect than LED light therapy performance for wound healing and cell proliferation in the related art.

In particular, the organic light-emitting device for light therapy for wound healing and cell proliferation according to the exemplary embodiment of the present invention can be driven at a low temperature to be safely closely contacted to a human body, and is thin, light, and is simply manufactured as compared with the related art to achieve convenience and reduce manufacturing cost.

According to the exemplary embodiment of the present invention, the organic light-emitting device for light therapy for wound healing and cell proliferation manufactures a red organic light-emitting device in a stacking structure including a heat sink layer to generate light in a form of a planar light source which can be driven at a low temperature, thereby solving a problem of a burn and can perform light therapy through close contact with the skin, have advantages such as thin, light, flexible, and inexpensive characteristics, and provide enhanced wound healing and cell proliferation effects compared with an LED in the related art.

DETAILED DESCRIPTION

The objects, specific advantages, and new features of the present invention will be more clearly understood from the following detailed description and the exemplary embodiments taken in conjunction with the accompanying drawings.

Terms or words used in the present specification and claims should not be interpreted as being limited to typical or dictionary meanings, but should be interpreted as having meanings and concepts which comply with the technical spirit of the present invention, based on the principle that an inventor can appropriately define the concept of the term to describe his/her own invention in the best manner.

In the present specification, when reference numerals refer to components of each drawing, it is to be noted that although the same components are illustrated in different drawings, the same components are denoted by the same reference numerals as possible.

The terms "first", "second", "one surface", "other surface", etc. are used to distinguish one component from another component and the components are not limited by the terms.

Hereinafter, in describing the present invention, a detailed description of related known art which may make the gist of the present invention unnecessarily ambiguous will be omitted.

Hereinafter, an exemplary embodiment of the present invention will be described in detail with reference to the accompanying drawings.

Figure 1:
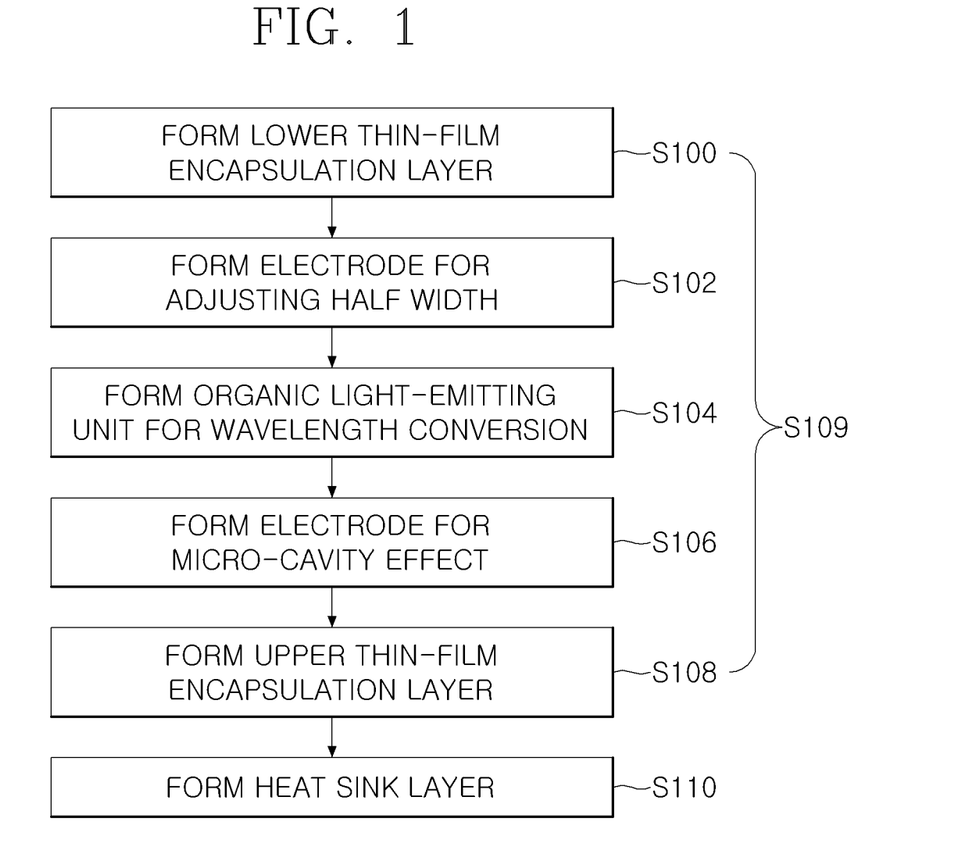
FIG. 1 is a flowchart of a manufacturing method of an organic light-emitting device for light therapy for wound healing and cell proliferation according to an exemplary embodiment of the present invention.
Figure 2:
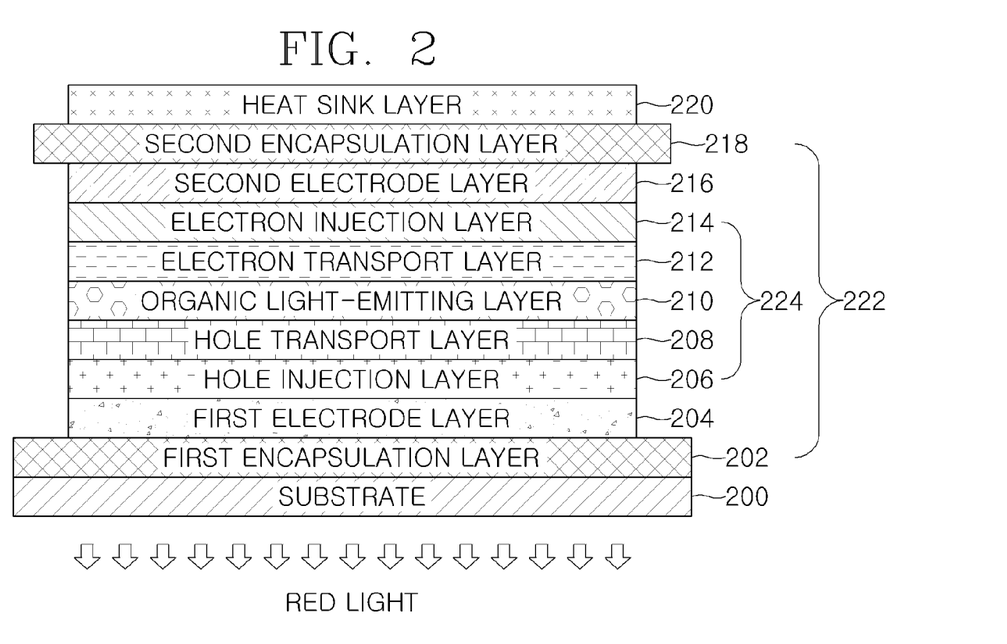
FIG. 2 is a cross-sectional view of an organic light-emitting device for light therapy for wound healing and cell proliferation according to an exemplary embodiment of the present invention.
Figure 3:
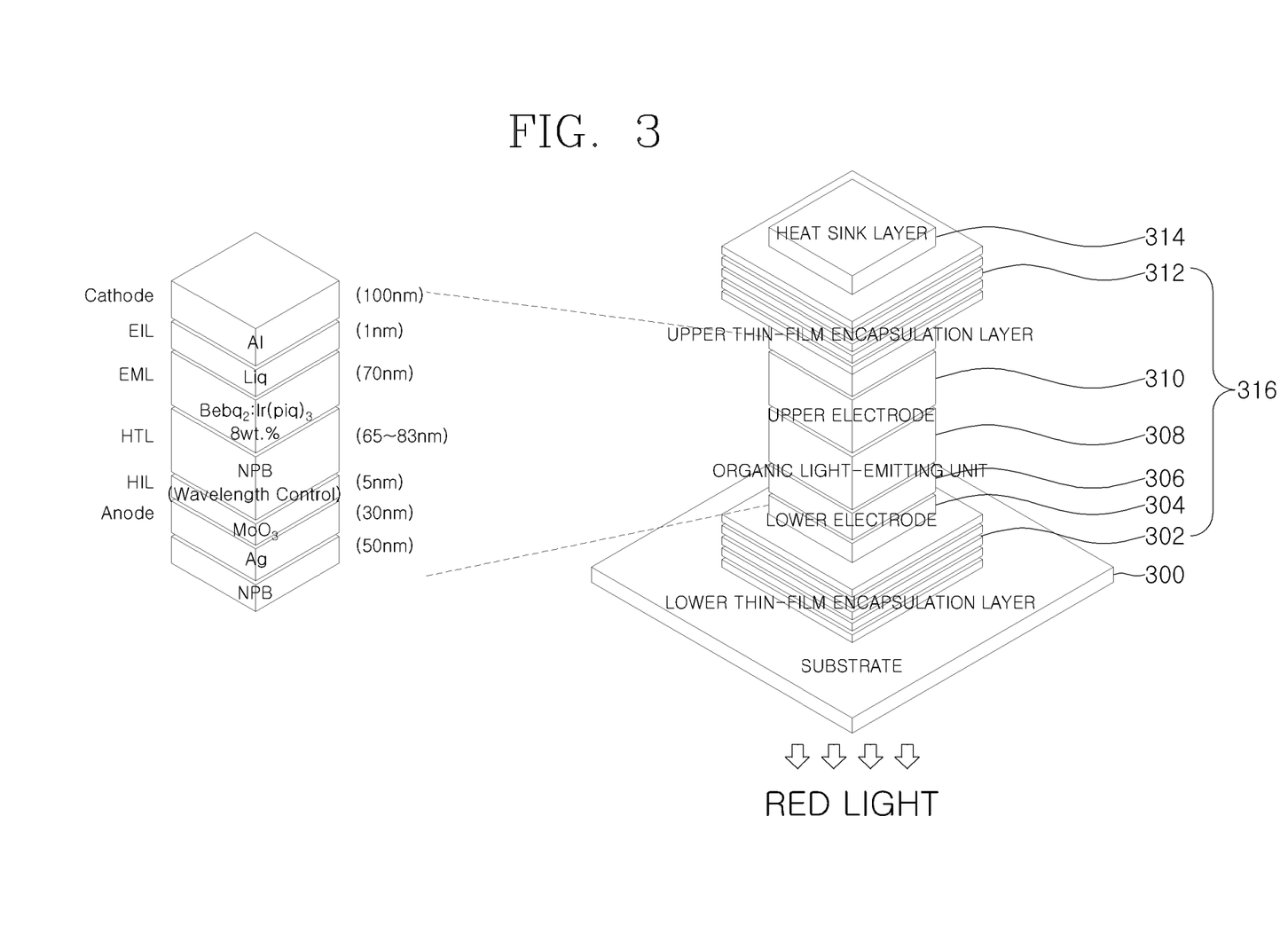
FIG. 3 is a diagram illustrating an organic light-emitting device for light therapy for wound healing and cell proliferation according to another exemplary embodiment of the present invention.

An organic light-emitting device for light therapy for wound healing and cell proliferation according to an exemplary embodiment of the present invention illustrated in FIGS. 2 and 3 is manufactured according to a flowchart of a manufacturing method of an organic light-emitting device for light therapy for wound healing and cell proliferation according to an exemplary embodiment of the present invention illustrated in FIG. 1.

The organic light-emitting device for light therapy for wound healing and cell proliferation according to an exemplary embodiment of the present invention illustrated in FIG. 2 includes a substrate 200, an organic light-emitting device layer 222 formed on the substrate 200 and emitting red light, and a heat sink layer 220 formed on the organic light-emitting device layer 222.

The organic light-emitting device for light therapy for wound healing and cell proliferation according to the exemplary embodiment of the present invention illustrated in FIG. 2 is a bottom emission organic light-emitting device outputting the red light generated by the organic light-emitting device layer 222 to the bottom.

The substrate 200 is made of a transparent material or a translucent material to output the red light generated by the organic light-emitting device layer 222 to the bottom.

The organic light-emitting device layer 222 includes a first encapsulation layer 202 as a lower thin-film encapsulation layer formed on the substrate 200, a first electrode layer 204 as a lower electrode formed on the first encapsulation layer 202, a hole injection layer 206 formed on the first electrode layer 204, a hole transport layer 208 formed on the hole injection layer 206, an organic light-emitting layer 210 formed on the hole transport layer 208 and emitting the red light, an electron transport layer 212 formed on the organic light-emitting layer, an electron injection layer 214 formed on the electron transport layer 212, a second electrode layer 216 as an upper electrode formed on the electron injection layer 214, and a second encapsulation layer 218 as an upper thin-film encapsulation layer formed on the second electrode layer 216.

The first electrode layer 204 is transparent or translucent, has a thickness of 10 to 100 nm, and is formed by one selected from a group consisting of Mg:Ag, Al, Cu, ITO, IZO, Mg, and Ca.

The hole transport layer 208 may be made of N,N'-Di(1-naphthyl)-N,N'-diphenyl-(1,1'-biphenyl)-4,4'-diamine (NPB) having a thickness of 50 to 100 nm and may be made of one selected from a group consisting of TCTA, TAPC, and mCP which are organic materials having similar refractive indexes and similar hole mobility.

A peak wavelength of the red light is changed according to the thickness of the hole transport layer 208.

Particularly, the peak wavelength of the red light generated by the organic light-emitting device layer 222 is adjusted appropriately for therapy by adjusting the thickness of the NPB which is the hole transport layer 208 between 65 nm and 83 nm so that the peak wavelength is arbitrarily adjusted within the range of 600 to 750 nm through a micro-cavity effect.

The organic light-emitting layer 210 has a thickness of 10 to 100 nm and emits the red light having a wavelength of 600 to 750 nm, and is made of one selected from a group consisting of $Ir(piq)_3$, $Ir(tiq)_3$, $Ir(fliq)_3$, $Ir(btpy)_3$, and $Ir(t-5t-py)_3$ which are the organic light-emitting materials having the similar refractive indexes.

In particular, in general, in the light therapy for wound healing and cell proliferation, a skin transmission length of the light source varies depending on the wavelength range of the light source and an absorbed wavelength area varies depending on a cell type and a cell tissue. Therefore, the organic light-emitting layer 210 is formed in a thickness of 70 nm by using a light-emitting layer phosphorescent material, such as Tris[1-phenylisoquinolinato-C2,N] iridium(III) ($Ir(piq)_3$) which emits the red light in the region of 600 to 750 nm, which is applied to various light therapy while light absorption is not interfered by hemoglobin and moisture.

The second electrode layer 216 has a thickness of 10 to 200 nm, totally reflects light, and is made of one selected from a group consisting of Mg:Ag, Al, Cu, Mg, and Ca.

The heat sink layer 220 has a thickness of 1 to 500 nm and is made of one selected from a group consisting of a carbon-based material, a metal-based material, and graphene.

According to the organic light-emitting device for light therapy for wound healing and cell proliferation according to the exemplary embodiment of the present invention configured as above, the red light generated by the organic light-emitting device layer 222 is output to the bottom through the substrate 200.

Figure 8:
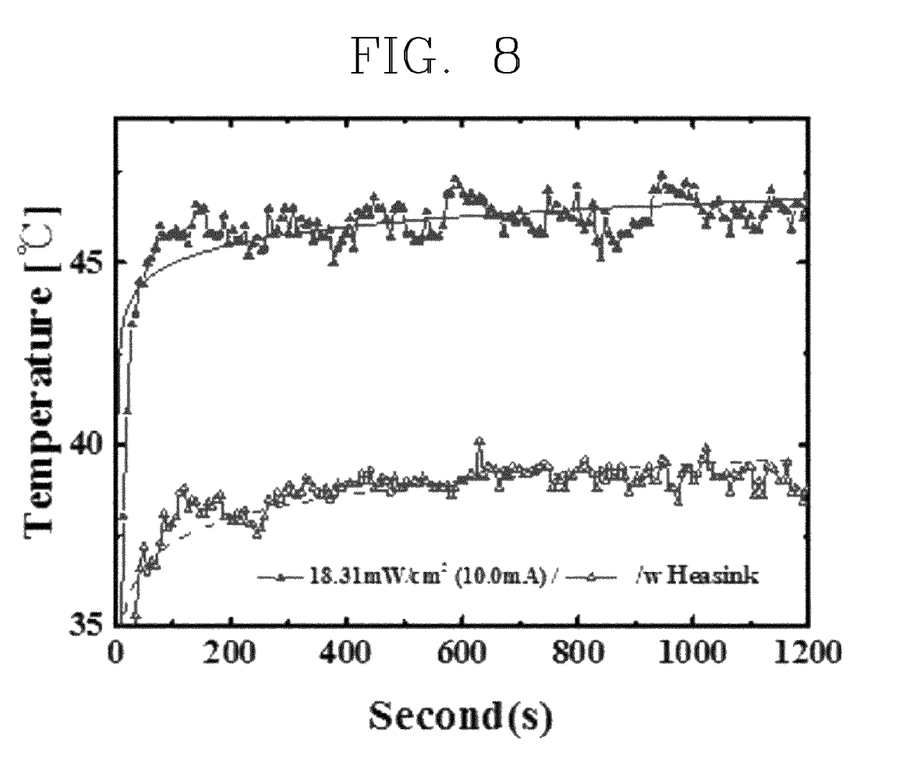
FIG. 8 is a diagram illustrating low-temperature driving using a heat sink layer of an organic light-emitting device for light therapy for wound healing and cell proliferation according to an exemplary embodiment of the present invention.

In the organic light-emitting device for light therapy for wound healing and cell proliferation according to the exemplary embodiment of the present invention, the heat sink layer 220 is stacked on the organic light-emitting device layer 222 to discharge heat generated from the organic light-emitting device layer 222 to the outside, thereby lowering a driving temperature to 42° C. or less as a low-temperature burn reference point as shown in a lower graph of FIG. 8. Meanwhile, an upper graph of FIG. 8 illustrates the driving temperature of the related art without the heat sink layer.

In the organic light-emitting device for light therapy for wound healing and cell proliferation according to the exemplary embodiment of the present invention, the heat sink layer 220 is formed on an opposite side to a direction in which the red light is output based on the organic light-emitting device layer 222. That is, as illustrated in FIG. 2, when the light is output to the bottom of the organic light-emitting device layer 222, the heat sink layer 220 is formed on the top of the organic light-emitting device layer 222. Therefore, when the light therapy is performed while the organic light-emitting device layer 222 and the substrate 200 on which the light is output closely contact the human body, the heat sink layer 220 may lower the driving temperature of the organic light-emitting device layer 222 by discharging the heat generated from the organic light-emitting device layer 222 to the outside without interfering with close contact therapy.

Since the organic light-emitting device for light therapy for wound healing and cell proliferation according to the exemplary embodiment of the present invention outputs the red light in the form of the surface light source and is driven at a low temperature to perform therapy in close contact with the human body unlike an LED light therapy method in the related art, the organic light-emitting device for light therapy for wound healing and cell proliferation may remarkably enhance the wound healing and cell proliferation effects.

Figure 6A:
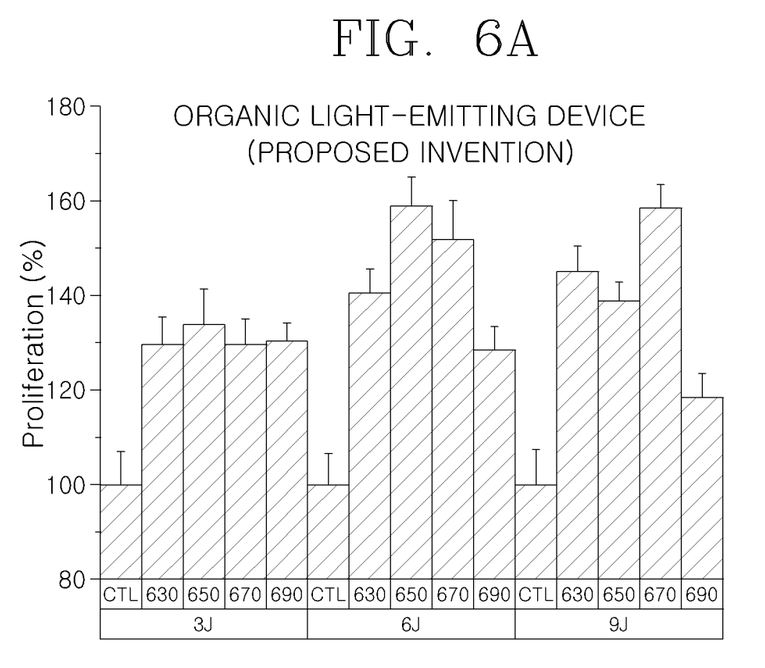
FIG. 6A is a diagram illustrating a cell proliferation effect of an organic light-emitting device for light therapy for wound healing and cell proliferation according to an exemplary embodiment of the present invention.
Figure 6B:
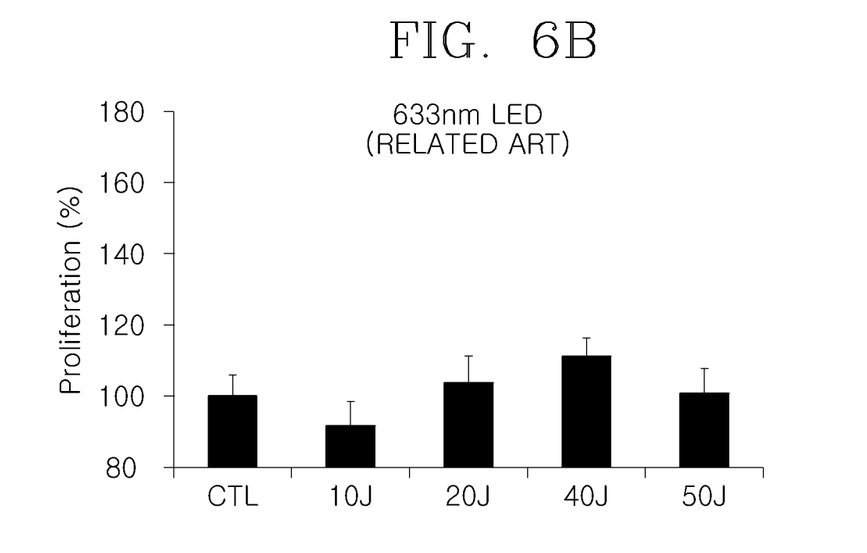
FIG. 6B is a diagram illustrating a cell proliferation effect in the related art.

Referring to FIG. 6A, the organic light-emitting device for light therapy for wound healing and cell proliferation according to the exemplary embodiment of the present invention apparently clearly shows the cell proliferation effect even at low irradiation energy and may be optimized to enhance the cell proliferation effect by up to 60% or more depending on the wavelength. This is an effect comparable to the cell proliferation effect (FIG. 6B) which is insignificant in a commercial 633 nm LED in the related art.

Figure 7A:
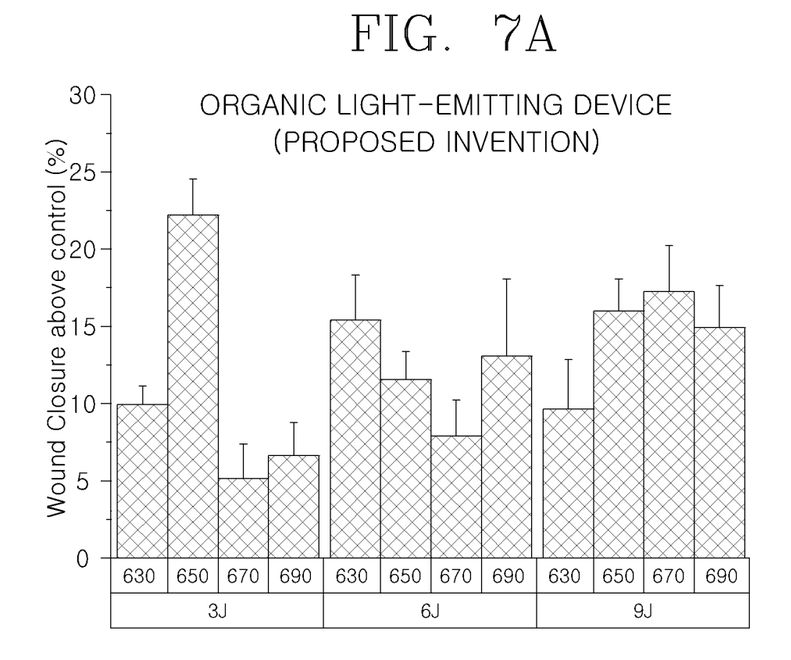
FIG. 7A is a diagram illustrating a wound healing effect of an organic light-emitting device for light therapy for wound healing and cell proliferation according to an exemplary embodiment of the present invention.
Figure 7B:
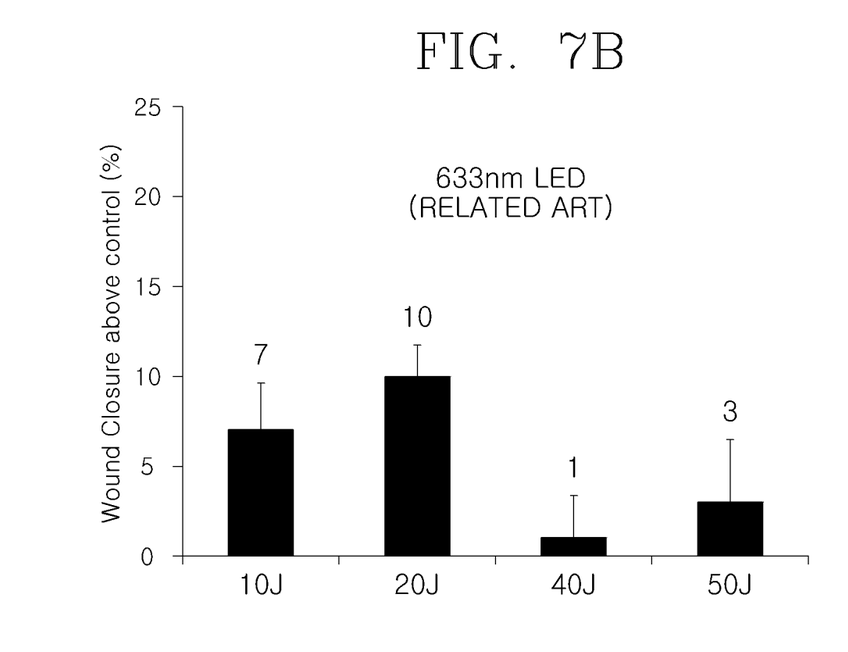
FIG. 7B is a diagram illustrating a wound healing effect in the related art.

Referring to FIG. 7A, the organic light-emitting device for light therapy for wound healing and cell proliferation according to the exemplary embodiment of the present invention apparently shows the wound healing effect even at the low irradiation energy and may optimize the wound healing effect depending on the wavelength. This is the wound healing effect that is enhanced compared to the commercial 633 nm LED (FIG. 7B) in the related art by 100% or more.

Meanwhile, the organic light-emitting device for light therapy for wound healing and cell proliferation according to another exemplary embodiment of the present invention illustrated in FIG. 3 is a bottom emission organic light-emitting device that includes a substrate 300, an organic light-emitting device layer 316 formed on the substrate 300, and a heat sink layer 314 formed on the organic light-emitting device layer 316 and outputs the red light generated by the organic light-emitting device layer 316 to the bottom.

The substrate 300 is made of the transparent material or the translucent material to output the red light generated by the organic light-emitting device layer 316 to the bottom.

The organic light-emitting device layer 316 includes a lower thin-film encapsulation layer 302 formed on the substrate 300, an optical capping layer 304 formed on the lower thin-film encapsulation layer 302, a lower electrode 306 formed on the optical capping layer 304, an organic light-emitting unit 308 formed on the lower electrode 306, an upper electrode 310 formed on the organic light-emitting unit 308, and an upper thin-film encapsulation layer 312 formed on the upper electrode 310. The optical capping layer 304 serves to allow the light emitted by the organic light-emitting unit 308 to pass downward without spreading.

In the organic light-emitting device for light therapy for wound healing and cell proliferation according to another exemplary embodiment of the present invention illustrated in FIG. 3, the organic light-emitting unit 308 has a structure in which an electron transport layer ETL (not illustrated) is integrated in an emission layer EML.

Meanwhile, a manufacturing method of an organic light-emitting device for light therapy for wound healing and cell proliferation according to an exemplary embodiment of the present invention will be described with reference to FIGS. 1 and 2.

The manufacturing method of the organic light-emitting device for light therapy for wound healing and cell proliferation according to an exemplary embodiment of the present invention illustrated in FIG. 1 includes forming the organic light-emitting device layer 222 emitting the red light onto the substrate 200 (step S109) and forming the heat sink layer 220 on the organic light-emitting device layer 222 (step S110). The substrate 200 is made of the transparent material or translucent material.

The manufacturing method of the organic light-emitting device for light therapy for wound healing and cell proliferation according to an exemplary embodiment of the present invention illustrated in FIG. 1 will be described in more detail.

In step S100, the first encapsulation layer 202 as the lower thin-film encapsulation layer is formed on the substrate 200 on which the organic light-emitting device for light therapy for wound healing and cell proliferation may be fabricated by using $Al_2O_3$ which is an inorganic material and a polymer film in order to protect the organic light-emitting device from moisture and oxygen.

In step S102, the first electrode layer 204 as the lower electrode of the organic light-emitting device is formed by thermally depositing metal silver on the first encapsulation layer 202 as large as a thickness of 30 nm as the lower thin-film encapsulation layer in order to control a half width of an emission wavelength for optimizing the light therapy.

In step S104, the organic light-emitting unit 224 for converting a wavelength and emitting the red light is formed on the first electrode layer 204.

In step S106, the second electrode layer 216 for a microcavity effect is formed on the organic light-emitting unit 224.

In step S108, the second encapsulation layer 218 which is the upper thin-film encapsulation layer is formed on the second electrode layer 216 by using $Al_2O_3$ which is the inorganic material and the polymer film in order to protect the organic light-emitting device from the moisture and the oxygen.

In step S110, the heat sink layer 220 is formed on the second encapsulation layer 218 in order to lower the driving temperature to a low temperature burn reference point of 42° C. or less by discharging the heat generated from the organic light-emitting device layer 222 to the outside.

In general, in the light therapy for wound healing and cell proliferation, the skin transmission length of the light varies depending on the wavelength range of the light source and the absorbed wavelength area varies depending on a cell type and a cell tissue. Therefore, in step S104, the organic light-emitting layer 210 is formed by forming a light-emitting layer phosphorescent material, such as Tris[1-phenylisoquinolinato-C2,N] iridium(III)(Ir(piq)$_3$) which emits the red light in the region of 600 to 750 nm, which is applied to various light therapy while light absorption is not interfered by hemoglobin and moisture, in a thickness of 70 nm.

However, since there are numerous endogenous chromatophores in the skin tissue, it is necessary to arbitrarily adjust the peak wavelength of the light source in order to treat a specific disease and optimize the effect of the treatment. Therefore, even if a Ir(piq)$_3$ emission layer is used as the organic light-emitting device, the peak wavelength is matched so as to apply the Ir(piq)$_3$ emission layer to various treatments.

Accordingly, when the organic light-emitting device layer 222 is formed, the peak wavelength of the red light generated by the organic light-emitting device layer 222 is adjusted appropriately for therapy by adjusting the thickness of the N,N'-Di(1-naphthyl)-N,N'-diphenyl-(1,1'-biphenyl)-4,4'-diamine (NPB) which is the hole transport layer (HTL) 208, etc., between 65 to 83 nm so as to arbitrarily adjust the peak wavelength of the light within the range of 600 to 750 nm through the micro-cavity effect.

Figure 4:
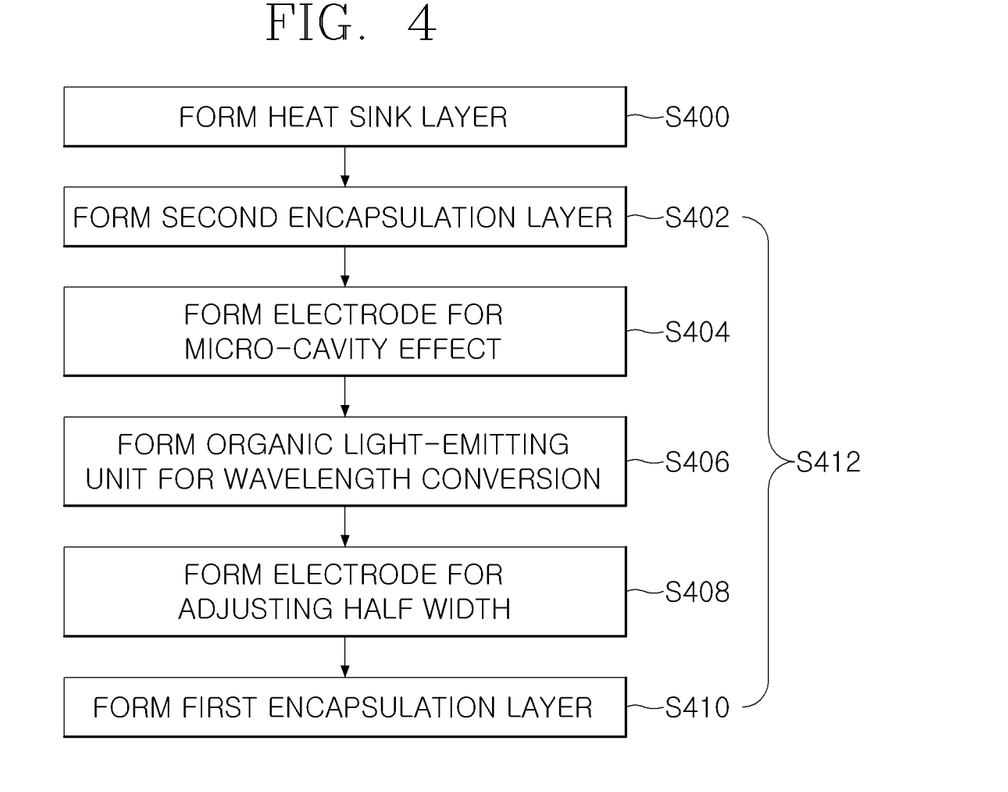
FIG. 4 is a flowchart of a manufacturing method of an organic light-emitting device for light therapy for wound healing and cell proliferation according to another exemplary embodiment of the present invention.
Figure 5:
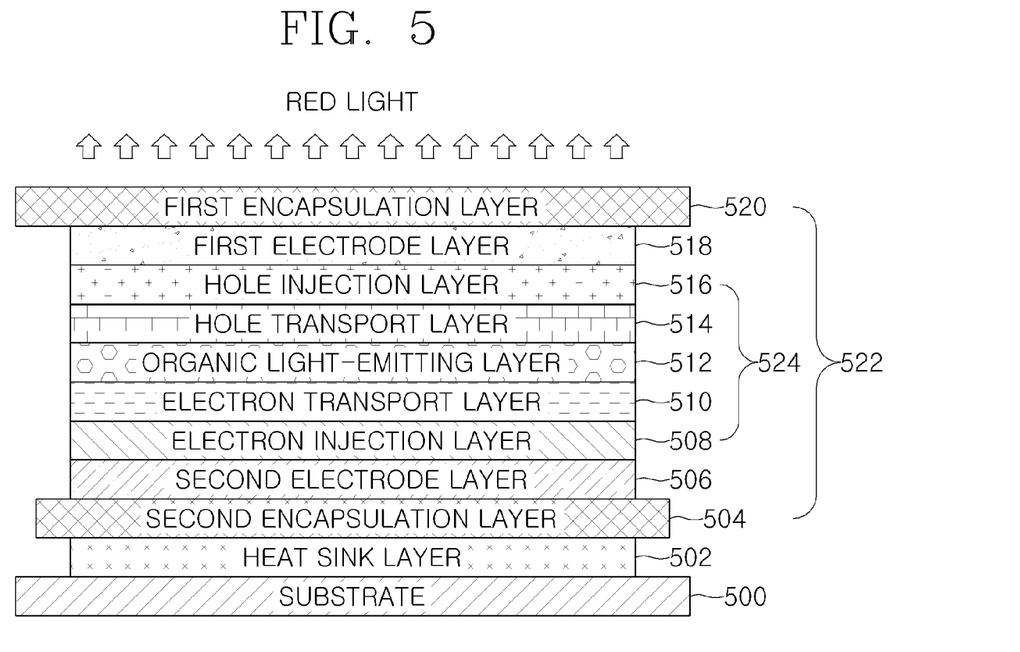
FIG. 5 is a cross-sectional view of an organic light-emitting device for light therapy for wound healing and cell proliferation according to another exemplary embodiment of the present invention.

Meanwhile, the organic light-emitting device for light therapy for wound healing and cell proliferation according to another exemplary embodiment of the present invention illustrated in FIG. 5 is manufactured according to the flowchart of the manufacturing method of the organic light-emitting device for light therapy for wound healing and cell proliferation according to another exemplary embodiment of the present invention illustrated in FIG. 4.

The organic light-emitting device for light therapy for wound healing and cell proliferation according to another exemplary embodiment of the present invention illustrated in FIG. 5 includes a substrate 500, a heat sink layer 502 formed on the substrate 500, and an organic light-emitting device layer 522 formed on the heat sink layer 502 and emitting the red light.

The organic light-emitting device for light therapy for wound healing and cell proliferation according to another exemplary embodiment of the present invention illustrated in FIG. 5 is a top emission organic light-emitting device outputting the red light generated by the organic light-emitting device layer 522 to the top.

The organic light-emitting device layer 522 includes a second encapsulation layer 504 formed on the heat sink layer 502, a second electrode layer 506 formed on the second encapsulation layer 504, an electron injection layer 508 formed on the second electrode 506, an electron transport layer 510 formed on the electron injection layer 508, an organic light-emitting layer 512 formed on the electron transport layer 510 and emitting the red light, a hole transport layer 514 formed on the organic light-emitting layer 512, a hole injection layer 516 formed on the hole transport layer 514, a first electrode layer 518 formed on the hole injection layer 516, and a first encapsulation layer 520 formed on the first electrode layer 518.

The first electrode layer 518 is transparent or translucent, has a thickness of 10 to 100 nm, and is formed by one selected from a group consisting of Mg:Ag, Al, Cu, ITO, IZO, Mg, and Ca.

The hole transport layer 514 may be made of N,N'-Di(1-naphthyl)-N,N'-diphenyl-(1,1'-biphenyl)-4,4'-diamine (NPB) having a thickness of 50 to 100 nm and may be made of one selected from a group consisting of TCTA, TAPC, and mCP which are organic materials having a similar refractive indexes and similar hole mobility.

The peak wavelength of the red light is changed according to the thickness of the hole transport layer 514.

Particularly, the peak wavelength of the red light generated by the organic light-emitting device layer 522 is adjusted appropriately for therapy by adjusting the thickness of the NPB which is the hole transport layer 514, etc., between 65 nm and 83 nm so as to arbitrarily adjust the peak wavelength within the range of 600 to 750 nm through the micro-cavity effect.

The organic light-emitting layer 512 has a thickness of 10 to 100 nm and emits the red light having a wavelength of 600 to 750 nm, and is made of one selected from a group consisting of Ir(piq)$_3$, Ir(tiq)$_3$, Ir(fliq)$_3$, Ir(btpy)$_3$, and Ir(t-5t-py)$_3$ which are the organic light-emitting materials having the similar refractive indexes.

In particular, in general, in the light therapy for wound healing and cell proliferation, the skin transmission length of the light source varies depending on the wavelength range of the light source and the absorbed wavelength area varies depending on a cell type and a cell tissue. Therefore, the organic light-emitting layer 512 is formed in a thickness of 70 nm by using a light-emitting layer phosphorescent material, such as Tris[1-phenylisoquinolinato-C2,N] iridium(III) (Ir(piq)$_3$) which emits the red light in the region of 600 to 750 nm, which is applied to various light therapy while light absorption is not interfered by hemoglobin and moisture.

The second electrode layer 506 has a thickness of 10 to 200 nm, totally reflects light, and is made of one selected from a group consisting of Mg:Ag, Al, Cu, Mg, and Ca.

The heat sink layer 502 has a thickness of 1 to 500 nm and is made of one selected from a group consisting of a carbon-based material, a metal-based material, and graphene.

According to the organic light-emitting device for light therapy for wound healing and cell proliferation according to another exemplary embodiment of the present invention configured as above, the red light generated by the organic light-emitting device layer 522 is output to the top.

In the organic light-emitting device for light therapy for wound healing and cell proliferation according to the exemplary embodiment of the present invention, the heat sink layer 502 is formed beneath the organic light-emitting device layer 522 to discharge heat generated from the organic light-emitting device layer 522 to the outside, thereby lowering the driving temperature to the low-temperature burn reference point, 42° C. or less as illustrated in FIG. 8.

In the organic light-emitting device for light therapy for wound healing and cell proliferation according to another exemplary embodiment of the present invention, the heat sink layer 502 is formed on an opposite side to a direction in which the red light is output based on the organic light-emitting device layer 522. That is, as illustrated in FIG. 5, when the light is output to the top of the organic light-emitting device layer 522, the heat sink layer 502 is formed on the bottom of the organic light-emitting device layer 522. Therefore, when the therapy is performed while the organic light-emitting device layer 522 closely contacts the human body, the heat sink layer 502 may lower the driving temperature of the organic light-emitting device layer 522 by dissipating the heat generated from the organic light-emitting device layer 522 to the outside without inferring with close contact therapy.

Since the organic light-emitting device for light therapy for wound healing and cell proliferation according to another exemplary embodiment of the present invention outputs the red light in the form of the surface light source and is driven at a low temperature to perform therapy in close contact with the human body unlike an LED light therapy method in the related art, the organic light-emitting device for light therapy for wound healing and cell proliferation may remarkably enhance the wound healing and cell proliferation effects.

Referring to FIG. 6A, the organic light-emitting device for light therapy for wound healing and cell proliferation according to the exemplary embodiment of the present invention apparently shows the cell proliferation effect even at low irradiation energy and may be optimized to enhance the cell proliferation effect by up to 60% or more depending on the wavelength. This is an effect comparable to the cell proliferation effect (FIG. 6B) which is insignificant in a commercial 633 nm LED in the related art.

Referring to FIG. 7A, the organic light-emitting device for light therapy for wound healing and cell proliferation according to the exemplary embodiment of the present invention apparently shows the wound healing effect even with the low irradiation energy and may optimize the wound healing effect depending on the wavelength. This is the wound healing effect that is enhanced compared to the commercial 633 nm LED (FIG. 7B) in the related art by 100% or more.

Meanwhile, a manufacturing method of an organic light-emitting device for light therapy for wound healing and cell proliferation according to another exemplary embodiment of the present invention will be described with reference to FIGS. 4 and 5.

The manufacturing method of the organic light-emitting device for light therapy for wound healing and cell proliferation according to another exemplary embodiment of the present invention illustrated in FIG. 4 includes forming the heat sink layer 502 on the substrate 500 (step S400) and forming the organic light-emitting device layer 522 emitting the red light onto the heat sink layer 502 (step S412).

The manufacturing method of the organic light-emitting device for light therapy for wound healing and cell proliferation according to another exemplary embodiment of the present invention illustrated in FIG. 4 will be described in more detail.

In step S400, the heat sink layer 502 is formed on the substrate 500 on which the organic light-emitting device for light therapy for wound healing and cell proliferation may be fabricated in order to lower the driving temperature to the low temperature burn reference point of 42° C. or less by discharging the heat generated from the organic light-emitting device layer 522 to the outside.

In step S402, the second encapsulation layer 504 is formed on the heat sink layer 502 by using $Al_2O_3$ which is the inorganic material and the polymer film in order to protect the organic light-emitting device from the moisture and the oxygen.

In step S404, the second electrode layer 506 for the micro-cavity effect is formed on the second encapsulation layer 504.

In step S406, the organic light-emitting unit 524 for converting the wavelength and emitting the red light is formed on the second electrode layer 506.

In step S408, the first electrode layer 518 is formed by thermally depositing the metal silver on the organic light-emitting unit 524 as large as the thickness of 30 nm in order to control the half width of the emission wavelength for optimizing the light therapy.

In step S410, the first encapsulation layer 520 is formed on the first electrode layer 518 by using $Al_2O_3$ which is the inorganic material and the polymer film in order to protect the organic light-emitting device from the moisture and the oxygen.

In general, in the light therapy for wound healing and cell proliferation, the skin transmission length of the light source varies depending on the wavelength range of the light source and the absorbed wavelength area varies depending on the cell type and the cell tissue. Therefore, in step S406, the organic light-emitting layer 512 is formed by forming a light-emitting layer phosphorescent material, such as Tris [1-phenylisoquinolinato-C2,N] iridium(III)(Ir(piq)$_3$) which emits the red light in the region of 600 to 750 nm, which is applied to various light therapy while light absorption is not interfered by hemoglobin and moisture, in the thickness of 70 nm.

However, since there are numerous endogenous chromatophores in the skin tissue, it is necessary to arbitrarily adjust the peak wavelength of the light source in order to treat the specific disease and optimize the effect of the treatment. Therefore, even if the Ir(piq)$_3$ emission layer is used as the organic light-emitting device, the peak wavelength is matched so as to apply the Ir(piq)$_3$ emission layer to various treatments.

Accordingly, when the organic light-emitting device layer 522 is formed, the peak wavelength of the red light generated by the organic light-emitting device layer 522 is adjusted appropriately for therapy by adjusting the thickness of the N,N'-Di(1-naphthyl)-N,N'-diphenyl-(1,1'-biphenyl)-4,4'-diamine (NPB) which is the hole transport layer (HTL) 514, etc., so as to arbitrarily adjust the peak wavelength of the light within the range of 6000 to 750 nm through the micro-cavity effect.

The organic light-emitting device for light therapy for wound healing and cell proliferation according to the exemplary embodiment of the present invention may be fabricated to enable bottom emission, top emission, and double-side emission according to an application method.

In the organic light-emitting device for light therapy for wound healing and cell proliferation according to the exemplary embodiment of the present invention, a glass encapsulation, a thin-film encapsulation, a metal encapsulation, or the like may be used to protect the organic light-emitting device from external environments such as moisture and oxygen.

In the organic light-emitting device for light therapy for wound healing and cell proliferation according to the exemplary embodiment of the present invention, in order to control the emission wavelength half width for optimizing the light therapy, metallic materials having various transmittances and various thicknesses may be utilized for the lower electrode layer or the upper electrode layer of the organic light-emitting device.

In the organic light-emitting device for light therapy for wound healing and cell proliferation according to the exemplary embodiment of the present invention, various organic light-emitting layer materials for emitting light having a wavelength of a region of 600 to 750 nm may be utilized, which are applied for various light therapy.

In the organic light-emitting device for light therapy for wound healing and cell proliferation according to the exemplary embodiment of the present invention, materials and thicknesses having various thermal conductivities may be utilized for the heat sink layer in order to lower the driving temperature of the organic light-emitting device to the low-temperature burn reference point (42° C.) or less.

The organic light-emitting device for light therapy for wound healing and cell proliferation according to the exemplary embodiment of the present invention is an invention relating to a light therapy apparatus using an organic light-emitting device which was not applied for the wound healing and cell proliferation effects in the related art may solve a disadvantage of an LED light therapy apparatus which is commercialized in the related art and maximize the wound healing and cell proliferation effects compared with the related art. In the organic light-emitting device for light therapy for wound healing and cell proliferation according to the exemplary embodiment of the present invention, the cell proliferation effect, which has hardly appeared in the LED therapy device in the related art, shows a more excellent effect by up to 60% or more compared with the LED device in the related art. An experimental result is shown, in which the wound healing effect of the organic light-emitting device for light therapy for wound healing and cell proliferation according to the exemplary embodiment of the present invention is superior to that of LED by 100% or more.

While the present invention has been particularly described with reference to detailed exemplary embodiments thereof, it is to specifically describe the present invention and the present invention is not limited thereto and it will be apparent that modification and improvement of the present invention can be made by those skilled in the art within the technical spirit of the present invention.

Simple modification and change of the present invention all belong to the scope of the present invention and a detailed protection scope of the present invention will be clear by the appended claims.

What is claimed is:

1. An organic light-emitting device for light therapy for wound healing and cell proliferation, comprising:
    a substrate;
    an organic light-emitting device layer formed on the substrate and emitting red light; and
    a heat sink layer formed on the organic light-emitting device layer,
    wherein the organic light-emitting device layer includes
        a first encapsulation layer formed on the substrate,
        a first electrode layer formed on the first encapsulation layer,
        a hole injection layer formed on the first electrode layer,
        a hole transport layer formed on the hole injection layer,
        an organic light-emitting layer formed on the hole transport layer and emitting red light,
        an electron transport layer formed on the organic light-emitting layer,
        an electron injection layer formed on the electron transport layer,
        a second electrode layer formed on the electron injection layer, and
        a second encapsulation layer formed on the second electrode layer,
    wherein the first electrode layer is transparent or translucent and the second electrode layer totally reflects light,
    wherein a thickness of the hole transport layer, via a micro cavity effect, changes a peak wavelength of the red light emitted from the organic light-emitting layer such that the wavelength of the red light emitted from the organic light-emitting device layer is different from the wavelength of the red light emitted from the organic light-emitting layer, and
    wherein the thickness of the hole transport layer is 65 to 83 nm and the peak wavelength of the red light emitted from the organic light-emitting device layer is 600 to 750 nm.

2. The organic light-emitting device of claim 1, wherein the substrate is transparent or translucent.

3. The organic light-emitting device of claim 1, wherein the organic light-emitting layer has a thickness of 10 to 100 nm and emits red light having a wavelength of 600 to 750 nm.

4. The organic light-emitting device of claim 3, wherein the organic light-emitting layer is made of one selected from a group consisting of Ir(piq)$_3$, Ir(tiq)$_3$, Ir(fliq)$_3$, Ir(btpy)$_3$, and Ir(t-5t-py)$_3$.

5. The organic light-emitting device of claim 1, wherein the heat sink layer has a thickness of 1 to 500 nm and is made of one selected from a group consisting of a carbon-based material, a metal-based material, and graphene.

6. The organic light-emitting device of claim 1, wherein the thickness of the hole transport layer is set such that the peak wavelength of the red light emitted from the organic light-emitting device layer is 630 to 750 nm.

7. An organic light-emitting device for light therapy for wound healing and cell proliferation, comprising:
    a substrate;
    a heat sink layer formed on the substrate; and
    an organic light-emitting device layer formed on the heat sink layer and emitting red light,
    wherein the organic light-emitting device layer includes
        a second encapsulation layer formed on the heat sink layer,
        a second electrode layer formed on the second encapsulation layer,
        an electron injection layer formed on the second electrode layer,
        an electron transport layer formed on the electron injection layer,
        an organic light-emitting layer formed on the electron transport layer and emitting red light,
        a hole transport layer formed on the organic light-emitting layer,
        a hole injection layer formed on the hole transport layer,
        a first electrode layer formed on the hole injection layer, and
        a first encapsulation layer formed on the first electrode layer,
    wherein the first electrode layer is transparent or translucent and the second electrode layer totally reflects light,
    wherein a thickness of the hole transport layer, via a micro cavity effect, changes a peak wavelength of the red light emitted from the organic light-emitting layer such that the wavelength of the red light emitted from the organic light-emitting device layer is different from the wavelength of the red light emitted from the organic light-emitting layer, and
    wherein the thickness of the hole transport layer is 65 to 83 nm and the peak wavelength of the red light emitted from the organic light-emitting device layer is 600 to 750 nm.

8. The organic light-emitting device of claim 7, wherein the organic light-emitting layer has a thickness of 10 to 100 nm and emits red light having a wavelength of 600 to 750 nm.

9. The organic light-emitting device of claim 8, wherein the organic light-emitting layer is made of one selected from a group consisting of Ir(piq)$_3$, Ir(tiq)$_3$, Ir(fliq)$_3$, Ir(btpy)$_3$, and Ir(t-5t-py)$_3$.

10. The organic light-emitting device of claim 7, wherein the heat sink layer has a thickness of 1 to 500 nm and is made of one selected from a group consisting of a carbon-based material, a metal-based material, and graphene.

11. The organic light-emitting device of claim 7, wherein the thickness of the hole transport layer is set such that the peak wavelength of the red light emitted from the organic light-emitting device layer is 630 to 750 nm.

12. A manufacturing method of an organic light-emitting device for light therapy for wound healing and cell proliferation, comprising:
    (a) forming an organic light-emitting device layer emitting red light on a substrate; and
    (b) forming a heat sink layer on the organic light-emitting device layer,
    wherein the forming of the organic light-emitting device layer includes (a-1) forming a first encapsulation layer on the substrate,
(a-2) forming a first electrode layer on the first encapsulation layer,
(a-3) forming a hole injection layer on the first electrode layer,
(a-4) forming a hole transport layer on the hole injection layer,
(a-5) forming an organic light-emitting layer emitting red light on the hole transport layer,
(a-6) forming an electron transport layer on the organic light-emitting layer,
(a-7) forming an electron injection layer on the electron transport layer,
(a-8) forming a second electrode layer on the electron injection layer, and
(a-9) forming a second encapsulation layer on the second electrode layer,
wherein the first electrode layer is transparent or translucent and the second electrode layer totally reflects light,
wherein a thickness of the hole transport layer, via a micro cavity effect, changes a peak wavelength of the red light emitted from the organic light-emitting layer such that the wavelength of the red light emitted from the organic light-emitting device layer is different from the wavelength of the red light emitted from the organic light-emitting layer, and
wherein the thickness of the hole transport layer is 65 to 83 nm and the peak wavelength of the red light emitted from the organic light-emitting device layer is 600 to 750 nm.

13. The method of claim 12, wherein the substrate is transparent or translucent.

14. The method of claim 12, wherein the thickness of the hole transport layer is set such that the peak wavelength of the red light emitted from the organic light-emitting device layer is 630 to 750 nm.

* * * * *